United States Patent
Leysieffer

[11] Patent Number: 6,154,677
[45] Date of Patent: Nov. 28, 2000

[54] IMPLANTABLE DEVICE WITH A CHARGING CURRENT FEED ARRANGEMENT WHICH HAS A RECEIVING COIL

[75] Inventor: Hans Leysieffer, Taufkirchen, Germany

[73] Assignee: IMPLEX Aktiengesellschaft Hearing Technology, Ismaning, Germany

[21] Appl. No.: 09/311,565

[22] Filed: May 14, 1999

[30] Foreign Application Priority Data

Aug. 20, 1998 [DE] Germany .............................. 198 37 913

[51] Int. Cl.⁷ ........................................................ A61N 1/08
[52] U.S. Cl. ............................................................... 607/61
[58] Field of Search ............................... 607/61, 33, 29, 607/27, 9

[56] References Cited

U.S. PATENT DOCUMENTS

| | | |
|---|---|---|
| 4,495,917 | 1/1985 | Byers . |
| 4,925,443 | 5/1990 | Heilman et al. . |
| 5,272,283 | 12/1993 | Kuzma . |
| 5,277,694 | 1/1994 | Leysieffer et al. . |
| 5,279,292 | 1/1994 | Baumann et al. . |
| 5,411,467 | 5/1995 | Hortmann et al. . |
| 5,702,431 | 12/1997 | Wang et al. . |
| 5,755,743 | 5/1998 | Volz et al. . |
| 5,814,095 | 9/1998 | Müller et al. . |

FOREIGN PATENT DOCUMENTS

| | | |
|---|---|---|
| 0 291 325 | 11/1988 | European Pat. Off. . |
| 33 11 507 | 5/1984 | Germany . |
| 196 45 371 | 12/1997 | Germany . |
| WO 94/08539 | 4/1994 | WIPO . |

*Primary Examiner*—Scott M. Getzow
*Attorney, Agent, or Firm*—Nixon Peabody LLP; David S. Safran

[57] ABSTRACT

Implantable device with a charging current feed arrangement (78) which has at least one receiving coil (106) into which energy can be fed electromagnetically via a charging device (59) located outside the body, an electrochemical battery (90) which can be repeatedly recharged via the charging current feed arrangement, and with a main module (56, 130) supplied with electric power by the battery. The components of the implantable device (54), with the exception of the receiving coil, are accommodated in a housing arrangement (72, 72', 72", 128, 132) of biocompatible metal. The receiving coil (106) is wound from at least one metallic conductor (109) that is jacketed with an electrically insulating material (11), is surrounded by a biocompatible polymer (104) and also is mechanically connected to at least part of the housing arrangement (72, 72', 72", 128, 132).

29 Claims, 5 Drawing Sheets

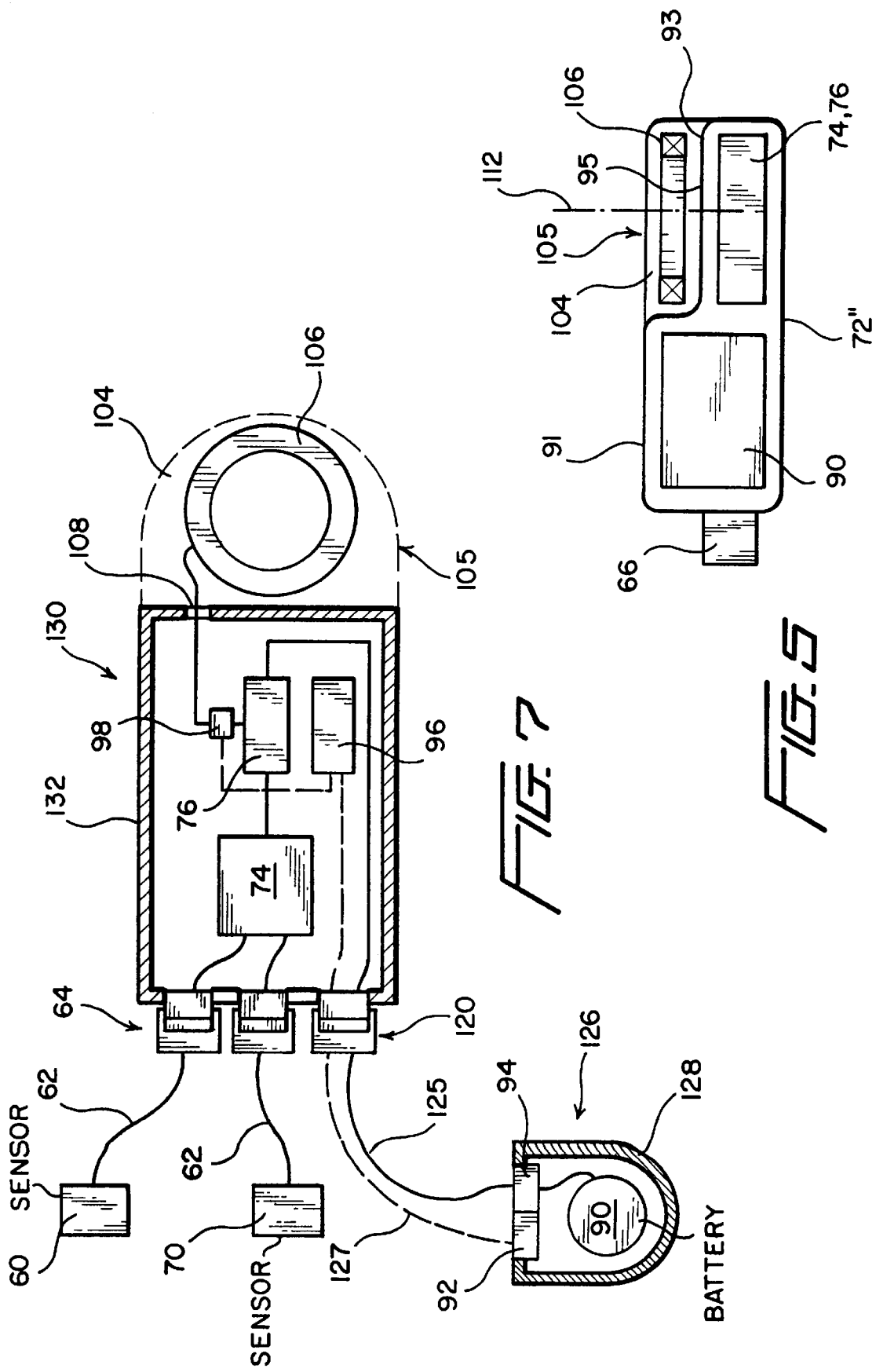

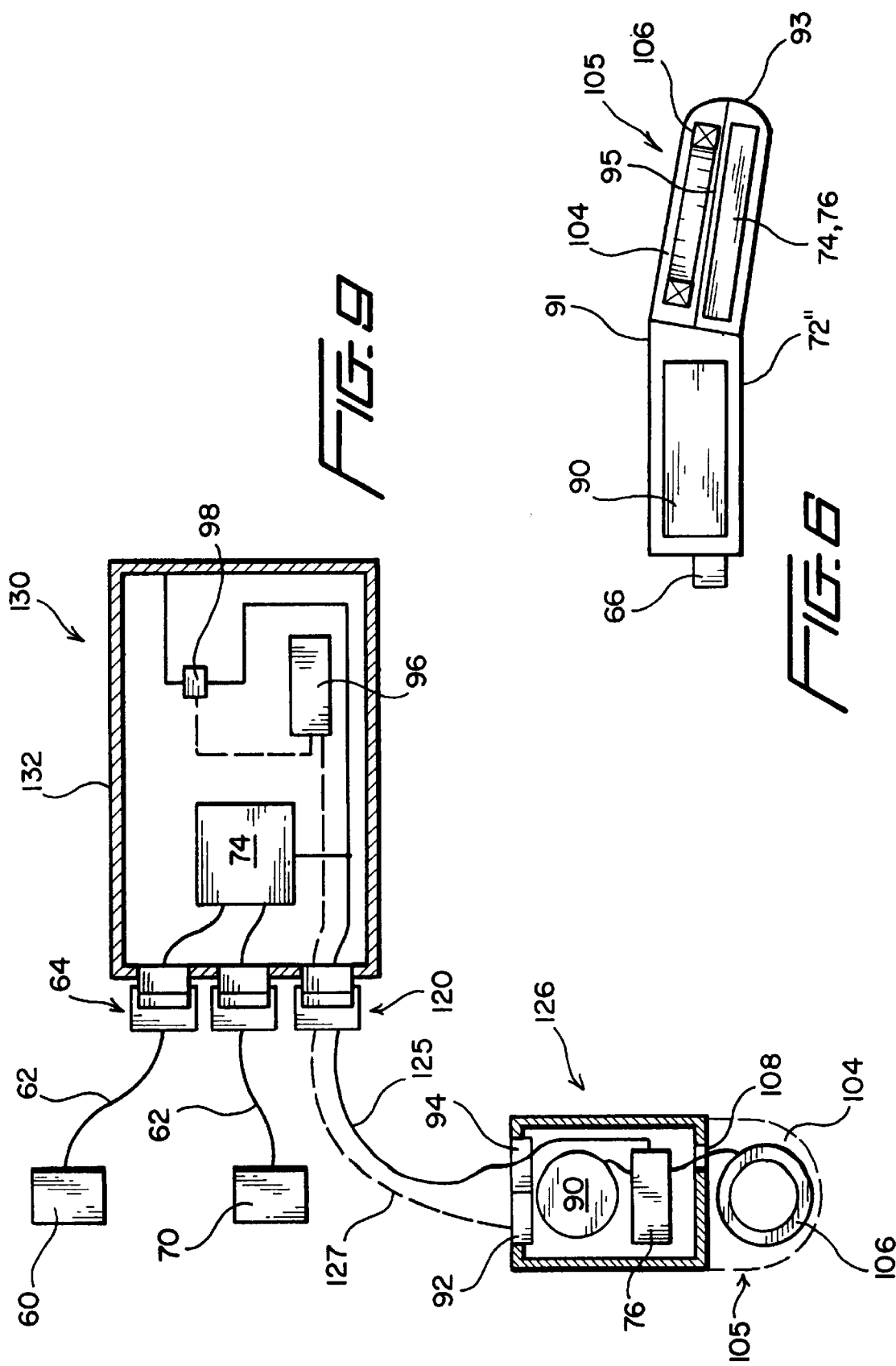

IMPLANTABLE DEVICE WITH A CHARGING CURRENT FEED ARRANGEMENT WHICH HAS A RECEIVING COIL

BACKGROUND OF THE INVENTION

1. Field of the Invention

The invention relates to an implantable device with a charging current feed arrangement having at least one receiving coil into which energy can be transcutaneously fed electromagnetically via a charging device located outside the body, with an electrochemical battery which can be repeatedly recharged via the charging current feed arrangement, and with a main module supplied by the battery with electric power, the components of the implantable device, with the exception of the receiving coil, being accommodated in a housing arrangement of biocompatible metal and the receiving coil sitting, outside the housing arrangement and being electrically coupled to the other part of the implantable device.

2. Description of Related Art

U.S. Pat. No. 5,279,292 discloses a hearing aid or tinnitus masker in which a main module and a power supply module with a rechargeable electrochemical battery can be accommodated in a common housing, or each can have its own separate housing, the common housing,or the housing of the power supply module also holding the receiving coil into which power can be electromagnetically supplied transcutaneously via the charging device located outside of the body. The implant housing(s) must be hermetically gas-tight. Therefore, for the housing containing the receiving coil, based on transcutaneous charging current feed, use can be made of ceramic materials, for example, $Al_2O_3$ or the like. However, ceramic housings are expensive and relatively sensitive to impact. This patent also describes an implantable device with a charging current feed arrangement, in which power is supplied percutaneously to a receiving coil located outside the implant housing; the receiving coil includes a ferrite core which extends through the skin. Any percutaneous arrangement, however, represents a potential source of infection or injury. The presence of an implant becomes disruptively visible from the outside. Nuclear spin tomographic studies of the implant wearer and the like are undesirably precluded by the ferrite core.

U.S. Pat. No. 5,702,431 discloses a transcutaneous recharging system for battery-powered implantable medical devices, especially defibrillators, in which a receiving coil of a charging current feed arrangement is located outside the device housing and is electrically coupled to the implantable device and in which the implantable device is accommodated in a titanium or stainless steel housing.

SUMMARY OF THE INVENTION

The object of the invention is to devise an implantable device which manages without a ceramic housing, but which is easy to handle for the implanting specialist nonetheless.

This object is achieved in accordance with the present invention in an implantable device by the receiving coil being wound from at least one metallic conductor jacketed with an electrically insulating material, surrounded by a biocompatible polymer, and also being mechanically connected to at least part of the housing arrangement.

In the case of the implantable device of the invention, the receiving coil of the charging current feed arrangement forms a structural unit with at least one part of the housing arrangement of the device which is convenient and easy to handle as a whole in the implantation process. At the same time, all requirements both for biocompatibility of the device and also suitability for transcutaneous transmission of electromagnetic energy for charging the battery can be satisfied without the need for an expensive and mechanically sensitive ceramic housing.

The implantable device can essentially be any implantable medical or biological device including, among others, an active electronic hearing implant, cardiac pacemaker, defibrillator, drug dispenser, nerve or bone growth stimulator, neurostimulator or retina stimulator, a pain suppression device or the like.

A hermetically tight execution of the metallic housing arrangement is preferred. Here, hermetic tightness is defined as preferably hermetic gas-tightness as per Mil-Std 883 D. This approach ensures that neither liquid nor gaseous substances can escape from the implanted housing arrangement or penetrate it.

Depending on the required dimensions of the components of the device and the spacial circumstances in the area of the implantation site, the receiving coil can be fixed on the outside of a metal housing which holds at least the main module or at least the battery.

A biocompatible polymer, preferably silicone, polyurethane, polyimide, polymethane, polytetrafluoroethylene (PTFE), parylene or the like, on the one hand, can be used to increase the mechanical cohesion of the coil itself, and on the other, can serve for mechanical coupling of the coil to the corresponding housing.

An especially compact structure can be obtained when the receiving coil is placed on at least a part of a broad side of the metal housing of the main module or the metallic outer or protective housing of the battery module. Advantageously, the coil axis of the receiving coil is at least roughly perpendicular to the broad side on which the coil is located.

Conversely, for especially effective transcutaneous power transmission, it is a good idea for the receiving coil to be located laterally bordering at least a part of the narrow side of the metal housing of the main module or the metallic outer or protective housing of the battery module, advantageously the coil axis of the receiving coil being at least roughly parallel to this narrow side.

The receiving coil can be flexible fixed on the metal housing of the main or battery module, resulting in the fact that the unit formed of the coil and housing can be geometrically better matched to the implantation site. Here, the flexible connection between the receiving coil and the pertinent housing is advantageously made of a biocompatible polymer, for which especially the polymers named above in conjunction with the jacketing of the receiving coil are suitable.

The conductor material of the receiving coil is preferably a biocompatible metallic material, especially a metal which is selected from the group consisting of gold, platinum, niobium, tantalum, iridium and their alloys. Gold, mainly pure gold, is especially well suited due to the combination of high electrical conductivity and outstanding biocompatibility. However, basically, as the conductor material for the receiving coil, there can also be a metal which, as such, is not biocompatible, for example, copper, when the biocompatibility of the entire arrangement is ensured in some other way, for example, by the jacket material of the receiving coil conductor and/or by the polymer which surrounds the receiving coil.

When the receiving coil is made as a coreless coil (air-core inductor), the implantable device can be kept entirely free of ferromagnetic materials. In this way, the implant carrier is not subject to any limitations, for example, with respect to nuclear spin tomography or the like.

In another embodiment of the invention, the receiving coil can be inclined at an angle in the range from 5 to 25° relative to the metal housing connected to it. This yields a unit formed of a coil and the corresponding housing which is especially well suited for implantation on the outside of the human skull, especially in the area of the mastoid plane, as is the case, for example, in at least partially implantable hearing aids, tinnitus maskers or retina stimulators and which has already been described in co-pending, commonly assigned, U.S. patent application Ser. No. 09/209,275.

It goes without saying that the battery can also supply electric power to one or more secondary modules which can be connected to the main module. Such secondary modules can be, for example, actuator and/or sensor components.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 5 shows a schematic cross section of a main module with assigned receiving coil according to a further modified embodiment;

FIG. 6 shows a schematic cross section similar to FIG. 5, but with an angled main module housing;

FIG. 7 is a schematic in section through another implantable device with the battery module flexibly coupled to the main module, the coil of the charging current feed arrangement being assigned to the main module;

FIG. 9 shows an embodiment similar to FIG. 8 in which the receiving coil is mechanically connected to the protective housing of the battery.

DETAILED DESCRIPTION OF THE INVENTION

Figure 1:
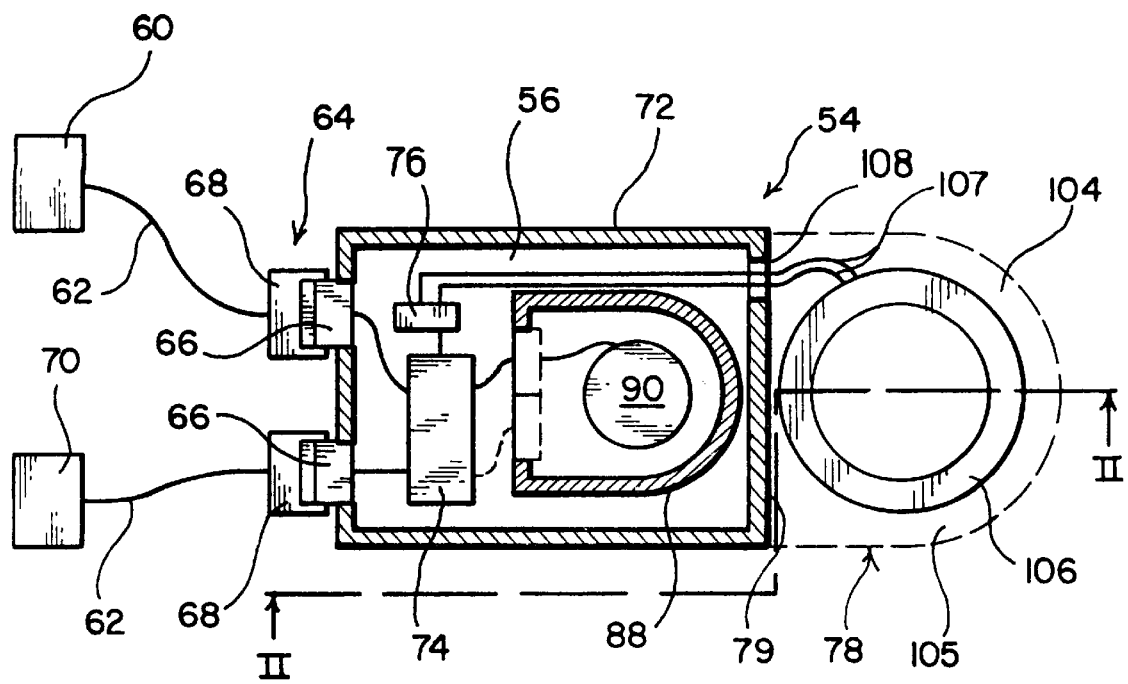
FIG. 1 shows a schematic in cross section through an implantable device with main and secondary modules, the coil of the charging current feed arrangement being assigned to the main module and being housed in a polymer jacket.

An implantable device labeled 54 in FIG. 1 comprises a main module 56, and as the secondary modules, a sensor 60 and an actuator component 70. The secondary modules 60 and 70 are each connected to the main module via a flexible connecting lead 62 and a coupling element labeled 64 as a whole. The secondary sensor module, in the case of an implantable hearing aid, can be a microphone, while the actuator secondary module can be an electromechanical converter which can be hydromechanically coupled to the liquid filled spaces of the inner ear or can be mechanically coupled to the ossicular chain, as is explained in U.S. Pat. Nos. 5,277,694; 5,411,467; and 5,814,095.

The coupling element 64 has a first half 66 assigned to the main module 56 and a secondary module-side, second half 68 which is detachably connected to the first half 66 and into which the flexible connecting lead 62 discharges. The coupling element 64 can especially be built in the manner known from U.S. Pat. No. 5,755,743 to provide for a preferably hermetically tight mutual connection within a small space. It goes without saying that all lines shown in simplified form in the figures, depending on the components which connect them, can be made in principle with one or several poles. The corresponding applies to the coupling elements and the line penetrations through the housing or housing parts.

Figure 10:
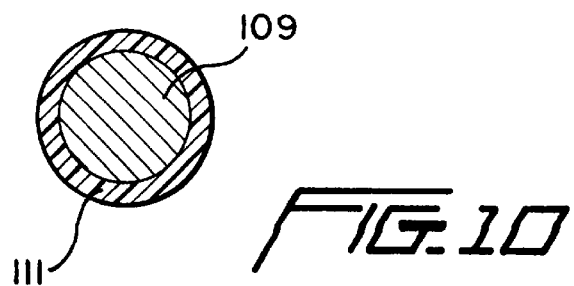
FIG. 10 shows a cross section of an insulated conductor of the receiving coil.

The main module housing 72 of the main module 56 holds signal processing electronics 74, charging/discharging electronics 76 and a rechargeable electrochemical battery 90 together with a protective housing 88 which is hermetically sealed and made of biocompatible metal. The signal processing electronics 74 control the actuator component 70 according to a stored program depending on the signals of the sensor component 60 and are connected to the two components via the coupling elements 64, which have first halves 66 which are integrated in a hermetically sealed manner into the main module housing 72. The charging/discharging electronics 76 form a nodal point between the signal processing electronics 74, the battery 90 and a charging current feed arrangement 78, and they are used for power distribution between these components. The charging current feed arrangement 78 includes, especially, a receiving coil 106 which can be inductively coupled for charging the battery 90 with the transmitting coil 57 of the charging device 59, the coil being located outside the body, as is known, for example, from U.S. Pat. No. 5,279,292. Optionally, the charging current feed arrangement 78 can contain other components which are not shown, for example, a capacitor for creating a tuned circuit. The receiving coil 106 is wound from a metallic conductor 109 (FIG. 10) surrounded with electrically insulating and preferably biocompatible material 111 and has an electrical resistance that is as low as possible, or from several such conductors and is potted with a biocompatible polymer 104, for example, a silicone.

Figure 2:
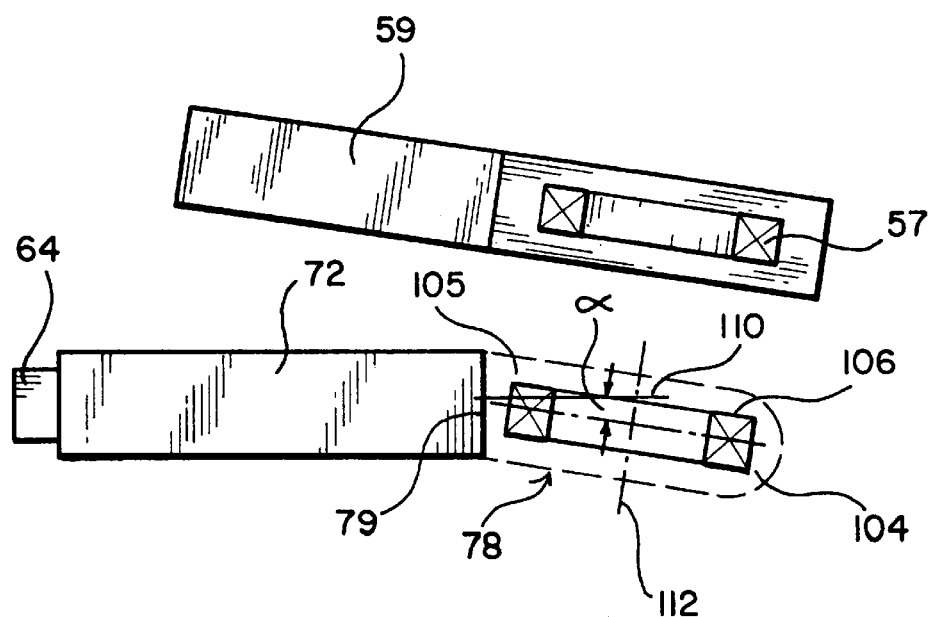
FIG. 2 shows a cross section of the main module taken along line II—II in FIG. 1 together with a charging device located outside the body.

The unit 105 comprised of the polymer jacketing 104 and the receiving coil 106 is connected mechanically tightly to the narrow side 79 of the metallic main module housing 72, that is, the side facing away from the coupling element 64, in the embodiment shown in FIGS. 1 and 2. For example, the unit 105 can be cemented to the main module housing 72. The polymer jacketing 104 can, however, also be molded or injection molded to the main module housing 72. The coil 106 is electrically connected to the charging/discharging electronics 76 via terminals 107 which are routed out of the main module housing 72 via a hermetically sealed penetration 108.

As illustrated in FIG. 2, for charging purposes, the transmitting coil 57 of the charging device 59 located outside the body is aligned with the receiving coil 106, and electromagnetic energy is transmitted transcutaneously from the transmitting coil to the receiving coil.

The narrow side 79 of the main module housing 72 is perpendicular to a straight line 110 which runs in the direction of the greatest extension of the housing 72. A straight line which runs perpendicular to the axis 112 of the coil 106 forms with the line 110 an angle α in the range from 5° to 25°, preferably in the range from 7° to 15°. This angling of the arrangement composed of the main module housing 72 and the unit 105 makes it possible, in the implantation of the device in a bone bed 75 formed on the outside of the skull 73 (FIG. 3), especially in the area of the mastoid plane, at a given size, especially depth, of the bone bed, to make available a comparatively large housing volume and at the same time to entirely or at least largely prevent the housing from projecting over the outside edge of the bone bed, as is explained in particular in the commonly assigned, co-pending U.S. patent application Ser. No. 09/209,275.

Figure 3:
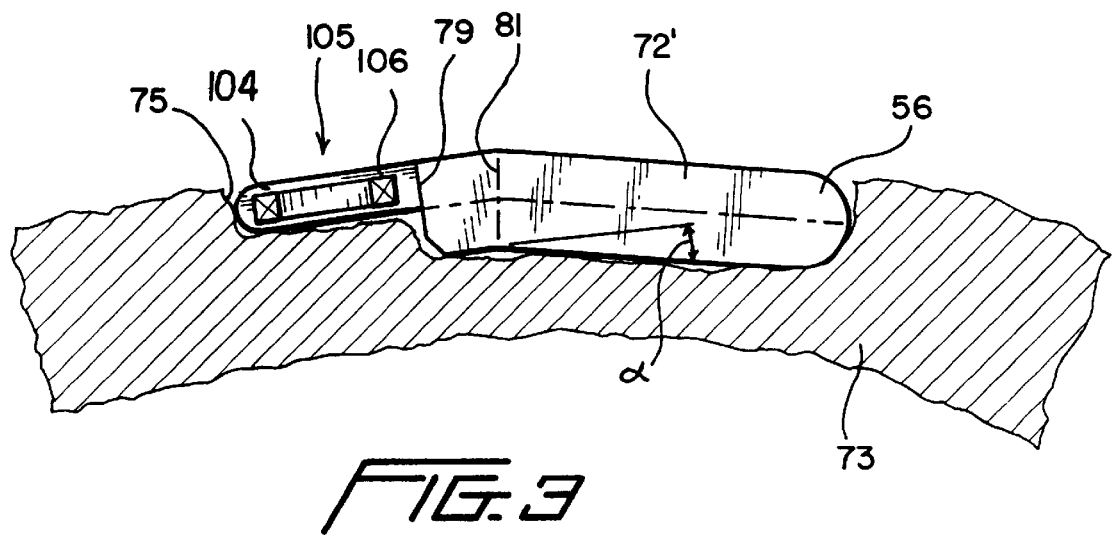
FIG. 3 shows a cross section similar to FIG. 2 for a modified embodiment of the main module in place in a skull.

While in the embodiment of FIGS. 1 and 2, the angling of the device 54 coincides with the short narrow side 79 of the housing, FIG. 3 shows an embodiment in which a corresponding angle site 81 is located in the area of the longitudinal extension of the housing 72' of the main module.

Figure 4:
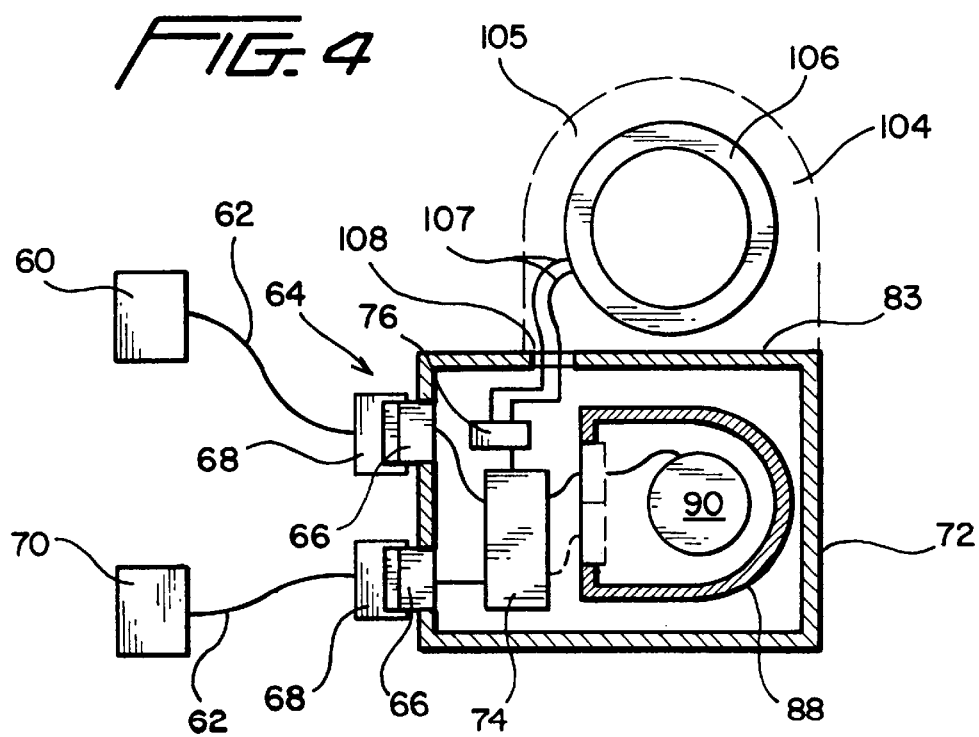
FIG. 4 shows an overhead view of a main module with a modified arrangement of the coil of the charging current feed arrangement.

The unit 105 comprised of the polymer jacketing 104 and the receiving coil 106 can also be attached to the main module housing 72 or 72' elsewhere than on the short narrow side 79. Thus, the plan view of FIG. 4 shows an embodiment in which the unit 105 is attached to the long narrow side 83 of the housing 72.

In practice, the chargeable battery 90 together with a protective system which is optionally assigned to the battery generally requires a vertical dimension which is larger than the necessary vertical dimension of the electronic modules 74 and 76 of the device. If in implantation it is a matter of the implant being especially compact with respect to its two other dimensions, i.e. the width and length dimensions, the arrangement can be advantageously made in the manner shown in FIGS. 5 & 6. Here, the main module housing 72" has a higher housing section 91 which is designed to hold the battery 90 and a housing section 93 which holds the electronic modules 74 and 76 with a height reduced compared to the housing section 91. In the area of the space formed by the housing gradation, the receiving coil 106 is attached, together with its polymer jacketing 104, on the wide side 95 of the lower housing section 93, the coil axis 112 being essentially perpendicular to the wide side 95. As shown, the unit 105 comprised of the receiving coil 106 and polymer jacketing 104 and the housing section 93, together, can have at least roughly the same height as the housing section 91. However, it must be considered that an arrangement of the unit 105 on, instead of next to, the metal housing 72" results in, during charging, the electromagnetic potential produced by the transmitting coil having to penetrate not only the receiving coil 106, but also the metallic housing parts. To prevent excess energy losses by eddy currents induced in the metallic housing parts, and thus undue heating of the metal housing, suitable countermeasures must be taken, for example, selection of a comparatively low frequency of the alternating field generated by the transmitting coil and/or minimization of the wall thickness of the housing wall parts penetrated by this field during charging.

According to FIG. 6, if desired, the housing section 93 together with the unit 105 can be angled relative to the housing section 91 similarly to that explained above relative to FIGS. 1 & 2 concerning the angling of the unit 105 relative to the housing 72.

In the embodiment shown in FIG. 7, the main module housing 132 of the main module 130, in addition to the signal processing electronics 74 and the charging/discharging electronics 76, holds evaluation electronics 96 and a switching element 98. The unit 105 comprised of the receiving coil 106 and the polymer jacketing 104 is attached to the main module housing 132. The battery 90, in this case, is accommodated in a hermetically sealed protective housing 128 of a battery module 126, the protective housing being separate from the main module housing 132. The protective housing 128 is made of biocompatible metal in the same manner as the main module housing 132. The battery module 126 is detachably connected via a power lead 125 and a coupling element, labeled 120 as a whole, to the charging/discharging electronics 76.

Between the battery 90 and the power lead 125, in this embodiment, there is a switching element 94 which is made as a break contact and which is fixed on the protective housing 128 and is mechanically activated by a detector element 92, for example, a deflectable membrane in an outside wall or partition of the protective housing 128, when a change in shape is impressed on the detector element 92 in an impermissible operating state of the battery 90. The detector element 92 is connected via a signal line 127 and the coupling element 120 to the evaluation electronics 96 which, for its part, is connected to the switching element 98. The evaluation electronics 96 monitors the state of the detector element 92 and depending thereon activates the switching element 98, which is made as a break contact and which is placed in the current path between the receiving coil 106 and the charging/discharging electronics 76. The state of the change in the shape of the detector element 92 is monitored, for example, via an electrical strain gauge. When a stipulated threshold shape change of the detector element 92 is exceeded, the switching element 98 interrupts further power supply from the unit 105 regardless of the function of the switching element 94 so that there is redundancy.

Figure 8:
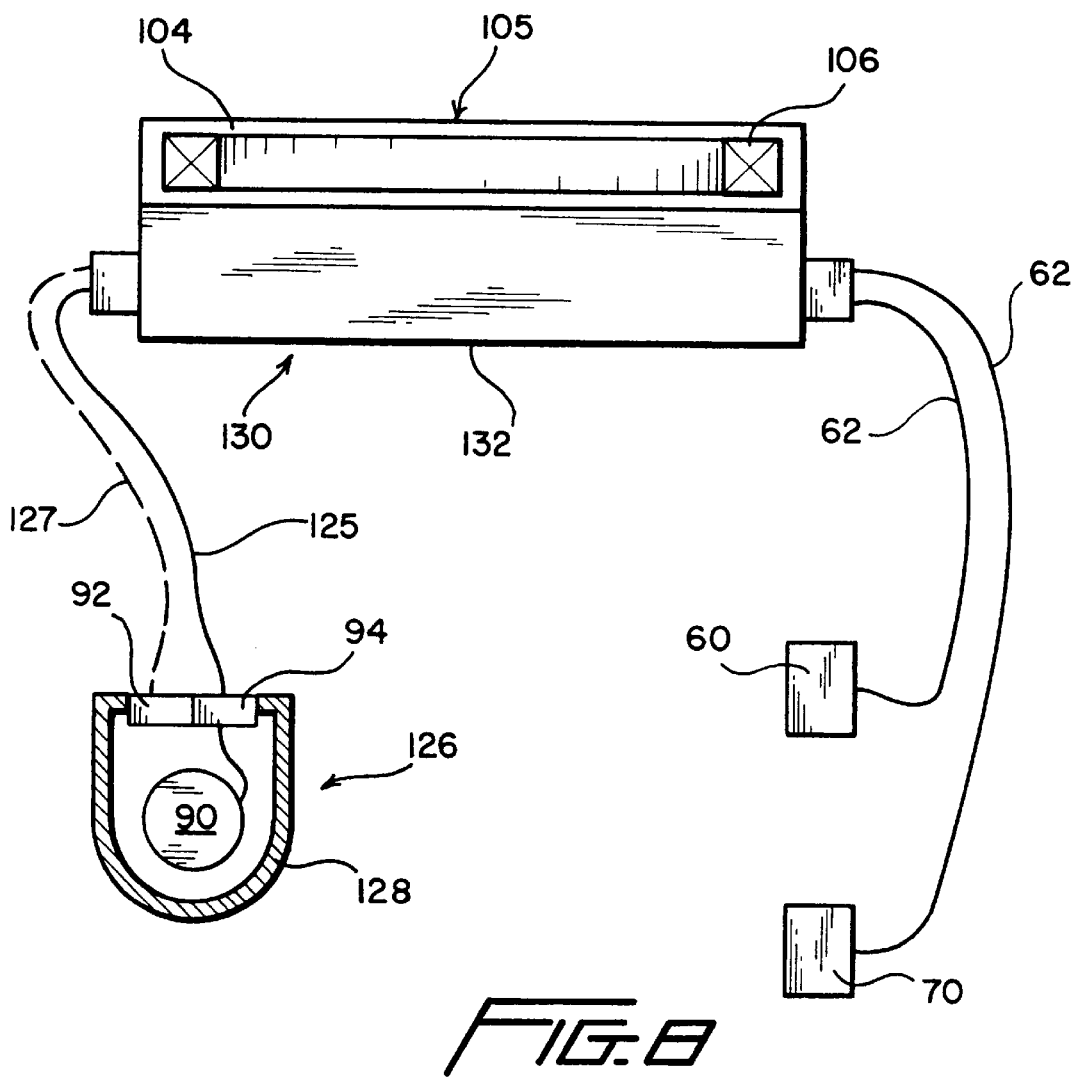
FIG. 8 shows a schematic of the main module of an implantable device with coil attached thereto and a battery module flexibly coupled to the main module.

The embodiment of FIG. 8 differs from that of FIG. 7 essentially only in that the receiving coil unit 105 is not attached laterally to the main module housing 132, but is seated on a broad side of the main module housing 132.

In the embodiment shown in FIG. 9, in contrast to the embodiments of FIGS. 7 & 8, the receiving coil unit 105 is not attached to the main module housing 132, but to the metallic protective housing 128 of the battery 90. Moreover, the charging/discharging electronics 76 are a component of the battery module 126. While in FIG. 9 a lateral attachment of the unit 105 to the protective housing 128 is shown, the unit 105 can also be placed, analogously to the arrangement shown in FIG. 8, on the broad side of the housing 128.

Within the framework of the invention, numerous other modifications and embodiments are possible. For example, the receiving coil can, optionally, also be used as the transmitting coil of a preferably bidirectional telemetry circuit in order, for example, to transcutaneously exchange information on the relative position of the receiving coil to the transmitting coil of the charging device and/or the charging state of the battery. For these purposes, a separate transmitting coil can be provided in addition to the receiving coil, if necessary. The transmitting coil likewise sitting outside the housing arrangement and being electrically coupled to the other part of the implantable device, is made of biocompatible metal, especially gold, surrounded by a biocompatible polymer and is mechanically connected to at least one part of the housing arrangement.

Thus, even though various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

I claim:

1. Implantable device with a charging current feed arrangement comprising:
    at least one receiving coil into which, in an implanted state within a body, energy can be transcutaneously fed electromagnetically via a charging device located externally of the body;
    a repeatedly rechargeable electrochemical battery; and
    a main module connected to the battery to receive electric power therefrom, and having a housing arrangement made of a biocompatible metal;
    wherein the receiving coil is located outside of the housing arrangement and being electrically coupled to the parts of the implantable device located within the housing arrangement;
    wherein the receiving coil is wound from at least one metallic conductor that is jacketed with an electrically insulating material and is surrounded by a biocompatible polymer; and
    wherein the receiving coil is mechanically connected to at least a part of the housing arrangement to form a unit therewith.

2. Implantable device as claimed in claim 1, wherein the metallic housing arrangement is made hermetically sealed.

3. Implantable device as claimed in claim 1, wherein the receiving coil is fixed on the outside of a metallic outer housing which holds at least the main module.

4. Implantable device as claimed in claim 1, wherein the receiving coil is fixed on the outside of a protective housing which holds at least the battery.

5. Implantable device as claimed in claim 4, wherein the receiving coil is fixed on the protective housing via the polymer which surrounds it.

6. Implantable device as claimed in claim 3, wherein the receiving coil is fixed on the metal housing via the polymer which surrounds it.

7. Implantable device as claimed claim 5, wherein the receiving coil is located on at least a part of a broad side of the housing arrangement of the main module.

8. Implantable device as claimed claim 3, wherein the receiving coil is located on at least a part of a broad side of the metallic outer housing.

9. Implantable device as claimed claim 4, wherein the receiving coil is located on at least a part of a broad side of the protective housing of the battery module.

10. Implantable device as claimed in claim 7, wherein the coil axis of the receiving coil is at least roughly perpendicular to the broad side of the housing arrangement of the main module.

11. Implantable device as claimed in claim 8, wherein the coil axis of the receiving coil is at least roughly perpendicular to the broad side of the of the metallic outer housing.

12. Implantable device as claimed in claim 9, wherein the coil axis of the receiving coil is at least roughly perpendicular to the broad side of the protective housing of the battery module.

13. Implantable device as claimed claim 5, wherein the receiving coil is located on at least a part of a narrow side of the housing arrangement of the main module.

14. Implantable device as claimed claim 3, wherein the receiving coil is located on at least a part of a narrow side of the metallic outer housing.

15. Implantable device as claimed claim 4, wherein the receiving coil is located on at least a part of a narrow side of the protective housing of the battery module.

16. Implantable device as claimed in claim 13, wherein the coil axis of the receiving coil is at least roughly parallel to the broad side of the housing arrangement of the main module.

17. Implantable device as claimed in claim 14, wherein the coil axis of the receiving coil is at least roughly parallel to the narrow side of the metallic outer housing.

18. Implantable device as claimed in claim 15, wherein the coil axis of the receiving coil is at least roughly parallel to the narrow side of the protective housing of the battery module.

19. Implantable device as claimed in claim 15, wherein the receiving coil is inclined at an angle in the range from 5° to 25° relative to the housing on which it is located.

20. Implantable device as claimed in claim 14, wherein the receiving coil is inclined at an angle in the range from 5° to 25° relative to the housing on which it is located.

21. Implantable device as claimed in claim 13, wherein the receiving coil is inclined at an angle in the range from 5° to 25° relative to the housing arrangement on which it is located.

22. Implantable device as claimed in claim 1, wherein the receiving coil is connected to the housing arrangement of the main module by a flexible connecting lead.

23. Implantable device as claimed in claim 11, wherein the flexible connecting lead between the receiving coil and the housing arrangement is comprised of a covering of biocompatible polymer.

24. Implantable device as claimed in claim 1, wherein the receiving coil has a conductor made of a biocompatible metal.

25. Implantable device as claimed in claim 1, wherein the conductor of the receiving coil is made from a metal which is chosen from the group consisting of gold, platinum, niobium, tantalum, iridium and their alloys.

26. Implantable device as claimed in claim 25, wherein the conductor of the receiving coil is made of pure gold.

27. Implantable device as claimed in claim 1, wherein said biocompatible polymer is chosen from the group consisting of silicones, polyurethanes, polyimides, polymethane, parylene, and polytetrafluoroethylene.

28. Implantable device as claimed in claim 23, wherein said biocompatible polymer is chosen from the group consisting of silicones, polyurethanes, polyimides, polymethane, parylene, and polytetrafluoroethylene.

29. Implantable device as claimed in claim 1, wherein the receiving coil is a coreless coil.

\* \* \* \* \*